US011793900B2

(12) United States Patent
Huitron et al.

(10) Patent No.: US 11,793,900 B2
(45) Date of Patent: Oct. 24, 2023

(54) SYSTEMS AND METHODS TO EMPLOY AN UNMANNED AERIAL VEHICLE TO SANITIZE A VEHICLE

(71) Applicant: Ford Global Technologies, LLC, Dearborn, MI (US)

(72) Inventors: Leonardo Alonso Huitron, Juarez (MX); Federico Emilio Mejia, Huixquilucan (MX); Gustavo Vazquez flores, Zumpango (MX); Hedy Humberto Morales Bolanos, Naucalpan (MX)

(73) Assignee: Ford Global Technologies, LLC, Dearborn, MI (US)

( * ) Notice: Subject to any disclaimer, the term of this patent is extended or adjusted under 35 U.S.C. 154(b) by 281 days.

(21) Appl. No.: 17/172,750

(22) Filed: Feb. 10, 2021

(65) Prior Publication Data

US 2022/0249722 A1    Aug. 11, 2022

(51) Int. Cl.
*A61L 2/24* (2006.01)
*B64C 39/02* (2023.01)
*B64U 101/00* (2023.01)

(52) U.S. Cl.
CPC .............. *A61L 2/24* (2013.01); *B64C 39/024* (2013.01); *A61L 2202/16* (2013.01); *A61L 2202/25* (2013.01); *B64U 2101/00* (2023.01); *B64U 2201/10* (2023.01)

(58) Field of Classification Search
CPC ........................ B64U 2101/70; B64U 2101/29
See application file for complete search history.

(56) References Cited

U.S. PATENT DOCUMENTS

| 2017/0121019 A1 | 5/2017 | Shin et al. |
| 2017/0285664 A1* | 10/2017 | Wang ..................... B64D 45/00 |
| 2018/0134412 A1* | 5/2018 | Poh ........................ B64F 1/0299 |

(Continued)

FOREIGN PATENT DOCUMENTS

WO    2016165793 A1    10/2016

OTHER PUBLICATIONS

Digital Aerolus—Aertos®120-UVC Industrial Drone Providing Remote UVC Disinfecting Capabilities for Indoor Areas, Reducing Health Risks.

*Primary Examiner* — Christian Chace
*Assistant Examiner* — Shayne M. Gilbertson
(74) *Attorney, Agent, or Firm* — Brandon Hicks; Eversheds Sutherland (US) LLP

(57) ABSTRACT

This disclosure is generally directed to systems and methods to sanitize a vehicle. In an example method, a motor vehicle wirelessly transmits a request to sanitize the motor vehicle. The request may be transmitted to an unmanned aerial vehicle (UAV) either directly or indirectly (via a server computer). The motor vehicle then detects the UAV landing upon the roof of the motor vehicle and opens a window of the motor vehicle. The UAV inserts an articulated arm through the open window and into the cabin area of the motor vehicle for executing a sanitizing procedure. The articulated arm can be configured to hold various objects such as a scrubbing pad and/or a container containing a cleaning agent, a sanitizing agent, or a deodorizing agent. In an example scenario, the sanitizing procedure may be directed at eliminating viruses and bacteria that may be present inside the cabin area of the motor vehicle.

19 Claims, 5 Drawing Sheets

(56) References Cited

U.S. PATENT DOCUMENTS

| | | | |
|---|---|---|---|
| 2019/0043370 A1* | 2/2019 | Mulhall | G08G 5/0026 |
| 2020/0231278 A1* | 7/2020 | Topaloglu | B60L 53/16 |
| 2020/0237941 A1 | 7/2020 | Bonutti et al. | |
| 2020/0269751 A1* | 8/2020 | Tatara | F21V 23/0478 |
| 2021/0322613 A1* | 10/2021 | Lacaze | G06N 20/00 |
| 2022/0024579 A1* | 1/2022 | Lee | A61L 9/20 |
| 2022/0234549 A1* | 7/2022 | Schütz | B60S 3/008 |
| 2022/0309473 A1* | 9/2022 | Weissbrich | B60L 53/65 |

\* cited by examiner

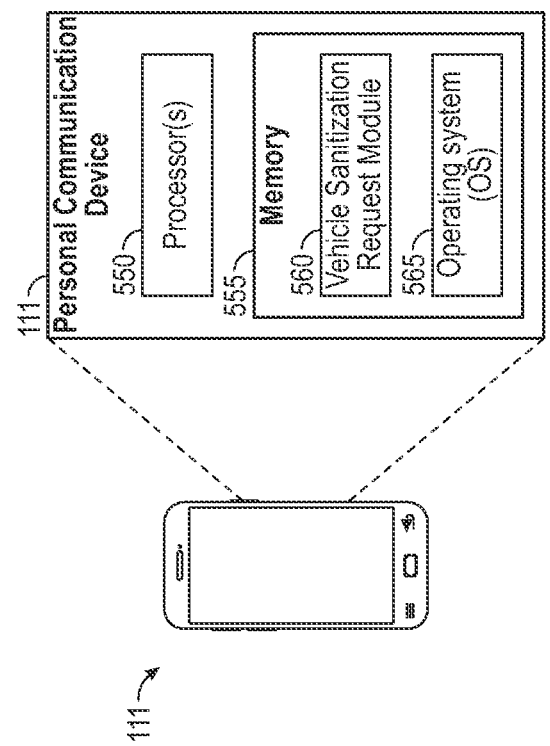

SYSTEMS AND METHODS TO EMPLOY AN UNMANNED AERIAL VEHICLE TO SANITIZE A VEHICLE

BACKGROUND

A ride hail (also called a ride share) vehicle may be occupied at various time by various people who may contribute to the spread of viruses. It may, however, be difficult for the driver of a ride share vehicle to sanitize the vehicle effectively due to cost and time constraints. It may be equally difficult in some cases for an individual vehicle owner to perform sanitizing operations upon his/her vehicle in a convenient and effective manner at various times and at various locations.

It is therefore desirable to provide a solution where a vehicle can be sanitized on request at any time and at any place.

BRIEF DESCRIPTION OF THE DRAWINGS

A detailed description is set forth below with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

FIG. 5 shows some example components that may be included in a personal communication device in accordance with an embodiment of the disclosure.

DETAILED DESCRIPTION

Overview

Figure 1:
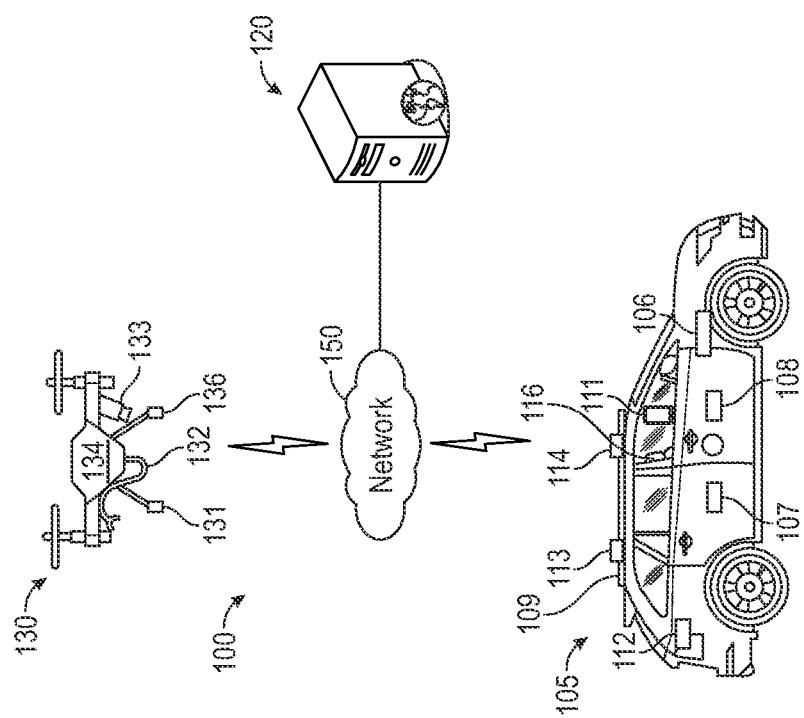
FIG. 1 shows an example system that includes an unmanned aerial vehicle (UAV) configured to sanitize a motor vehicle in accordance with an embodiment of the disclosure.

In terms of a general overview, certain embodiments described in this disclosure are directed to systems and methods related to sanitizing a vehicle. In an example method, a motor vehicle (e.g., an ICE, EV, and/or hybrid vehicle) wirelessly transmits a request to sanitize the motor vehicle. The request may be transmitted to an unmanned aerial vehicle (UAV) either directly or indirectly (via a server computer). The motor vehicle then detects the UAV landing upon the roof of the motor vehicle and opens a window of the motor vehicle. The UAV inserts an articulated arm through the open window and into the cabin area of the motor vehicle for executing a sanitizing procedure. The articulated arm can be configured to hold various objects such as a scrubbing pad and/or a container containing a cleaning agent, a sanitizing agent, or a deodorizing agent. In an example scenario, the sanitizing procedure may be directed at eliminating viruses and bacteria that may be present inside the cabin area of the motor vehicle.

Illustrative Embodiments

The disclosure will be described more fully hereinafter with reference to the accompanying drawings, in which example embodiments of the disclosure are shown. This disclosure may, however, be embodied in many different forms and should not be construed as limited to the example embodiments set forth herein. It will be apparent to persons skilled in the relevant art that various changes in form and detail can be made to various embodiments without departing from the spirit and scope of the present disclosure. Thus, the breadth and scope of the present disclosure should not be limited by any of the above-described example embodiments but should be defined only in accordance with the following claims and their equivalents. The description below has been presented for the purposes of illustration and is not intended to be exhaustive or to be limited to the precise form disclosed. It should be understood that alternate implementations may be used in any combination desired to form additional hybrid implementations of the present disclosure. For example, any of the functionality described with respect to a particular device or component may be performed by another device or component. Furthermore, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments.

Certain words and phrases are used herein solely for convenience and such words and terms should be interpreted as referring to various objects and actions that are generally understood in various forms and equivalencies by persons of ordinary skill in the art. For example, it must be understood that words such as "sanitize" and "sanitizing" as used herein are intended to encompass various other words such as "clean," "cleaning," "disinfect." "disinfecting," "wash," and "washing." In general, and in accordance with disclosure, these words pertain to removal of undesirable pollutants such as, for example, dirt, dust, debris, stains, spills, viruses, and bacteria that may be present in a motor vehicle. It should also be understood that the word "example" as used herein is intended to be non-exclusionary and non-limiting in nature.

FIG. 1 shows an example system 100 that includes an unmanned aerial vehicle (UAV) 130 configured to sanitize a motor vehicle 105 in accordance with an embodiment of the disclosure. The motor vehicle 105 may be any of various types of vehicles such as, for example, a car, a van, a sports utility vehicle, a truck, an electric vehicle, a gasoline vehicle, a hybrid vehicle, a driver-operated vehicle or an autonomous vehicle. The motor vehicle 105 may include components such as a vehicle computer 106, a vehicle sanitizer system 108, a pollutant detection system 107, and a wireless communication system 112. The components, which are symbolically depicted as black boxes in FIG. 1, may be installed at various locations on the motor vehicle 105, such as, for example, an engine compartment, a glove compartment, a trunk, and/or a console inside the cabin area.

The vehicle computer 106 may perform various functions such as, for example, controlling engine operations (fuel injection, speed control, emissions control, braking, etc.), managing climate controls (air conditioning, heating etc.), activating airbags, and issuing warnings (check engine light, bulb failure, low tire pressure, vehicle in blind spot, etc.). In some cases, the vehicle computer 106 may include more than one computer such as, for example, a first computer that controls engine operations and a second computer that operates the infotainment system.

The vehicle sanitizer system 108 is configured to execute various operations in accordance with the disclosure. Such operations may include cooperating with the wireless communication system 112 to wirelessly communicate with various systems and devices via a network 150. The network 150 may include any one, or a combination of networks, such as a local area network (LAN), a wide area network (WAN), a telephone network, a cellular network, a cable network, a wireless network, and/or private/public networks such as the Internet. For example, the network 150 may support communication technologies such as Bluetooth®, cellular, near-field communication (NFC), Wi-Fi, Wi-Fi direct, machine-to-machine communication, and/or man-to-machine communication. At least one portion of the network 150 includes a wireless communication link that allows the vehicle sanitizer system 108 to communicate via the wireless communication system 112 with the UAV 130 and/or other devices such as a server computer 120.

The pollutant detection system 107 may be implemented in any of various ways. In an example implementation, the pollutant detection system 107 can include multiple cameras that are mounted at various locations in a cabin area of the motor vehicle 105. The cameras are configured to capture images of various objects located in the cabin area such as, for example, the seats, the dashboard, the steering wheel, and other fixtures. In some cases, the cameras may capture images of one or more occupants present in the cabin area of the motor vehicle 105 (clothes, face, body, limbs, etc.). The images are conveyed to the vehicle sanitizer system 108, which may evaluate the images for detecting various undesirable elements (dirt, stains, etc.) that may be present on one or more of the various objects present in the cabin area of the motor vehicle 105.

The pollutant detection system 107 may further include one or more sensors mounted at various locations in a cabin area of the motor vehicle 105. The sensors may be selected and configured for capturing data pertaining to various types of undesirable elements that may be present in the air, on objects, and/or on individuals in the cabin area of the motor vehicle 105. In an example implementation, a first sensor may be selected and configured to detect biological pollutants such as, for example, viruses and/or bacteria. A second sensor may be selected and configured to detect chemical pollutants. Data provided by the sensors to the vehicle sanitizer system 108 may be evaluated by the vehicle sanitizer system 108 for detecting a presence, and/or level, of such pollutants if present in the cabin area of the motor vehicle 105.

The UAV 130 can include various components that may be used to sanitize the motor vehicle 105 upon receiving a sanitizing request from the vehicle sanitizer system 108 of the motor vehicle 105. The various components may include a camera 133 configured to capture images of the motor vehicle 105 and various other terrestrial objects. The images may be evaluated by a vehicle sanitizer service system 134 provided in the UAV 130. Evaluation of the images may be performed for various purposes such as, for example, to identify the motor vehicle 105 and to land on a landing pad 109 provided on the roof of the motor vehicle 105.

In an example implementation, the vehicle sanitizer service system 134 of the UAV 130 may cooperate with a communication system (not shown) in the UAV 130, to wirelessly communicate with the server computer 120 and/or the vehicle sanitizer system 108 of the motor vehicle 105 to obtain vehicle identification and/or vehicle location information of the motor vehicle 105. The vehicle identification can include information such as, for example, a make and a model of the motor vehicle 105 (Ford, Mustang, for example). The vehicle location may be provided in various forms such as for example, in the form of GPS coordinates and/or an address (residence, office, business, parking lot, street, road etc.).

In an example scenario, the UAV 130 may receive a sanitizing request from the motor vehicle 105. The sanitizing request may be transmitted autonomously by the vehicle sanitizer system 108 (when the motor vehicle 105 is an autonomous vehicle) or may be transmitted from a personal communication device 111 operated by a driver 116 of the motor vehicle 105 (when the motor vehicle 105 is a driver-operated vehicle). The personal communication device 111 can be any of various devices such as, for example, a smartphone, a tablet computer, a phablet (phone plus tablet computer), a laptop computer, or a smart device such as a smart watch.

The UAV 130 may respond to the sanitizing request by taking off from a launch site such as, for example, a warehouse, a commercial establishment, a business location, a service center, and/or from a mobility service (such as one or more vehicles, including cars, vans, buses, etc. or other transit or transportation services) to reach any destination. The UAV 130 may then utilize vehicle location information to fly to a rendezvous spot at which the motor vehicle 105 may be located at a rendezvous time. In an example implementation, the rendezvous time may be included in the sanitizing request and may be based on input information provided to the vehicle sanitizer system 108 by a driver of the motor vehicle 105 (if the motor vehicle 105 is a driver-operated vehicle) or generated autonomously by the vehicle sanitizer system 108 (if the motor vehicle 105 is an autonomous vehicle). The driver may determine the rendezvous time based on personal convenience such as, for example, after reaching a suitable spot, or after traveling to and parking the motor vehicle 105 at a parking lot at work or on a driveway at home, etc. An autonomous vehicle may determine the rendezvous time based on autonomous travel information (route, travel time, current location, desired destination for sanitizing purposes, etc.).

Upon reaching the rendezvous spot, the UAV 130 may evaluate images captured by the camera 133 to identify the motor vehicle 105 by using vehicle identification information including items such as the make, the model, and/or vehicle license plate.

After confirming the identity of the motor vehicle 105, the UAV 130 may land upon the landing pad 109 on the roof the motor vehicle 105. In an example implementation, the landing pad 109 can include one or more electromagnetic latches configured to attach to one or more electromagnetic latches in a landing gear of the UAV 130. In the example illustration, the motor vehicle 105 includes an electromagnetic latch 113 that is configured to attach to an electromagnetic latch 131 in a landing gear of the UAV 130, and another electromagnetic latch 114 that is configured to attach to another electromagnetic latch 136 in the landing gear of the UAV 130.

The electromagnetic latch 113 and electromagnetic latch 114 may be activated under control of the vehicle sanitizer system 108 in the motor vehicle 105 when the UAV 130 lands on the roof of the motor vehicle 105. The landing pad 109 may further include a sensor (such as weight sensor, for example) and/or a camera (not shown) that provide data and/or images to the vehicle sanitizer system 108 for evaluation to detect the landing of the UAV 130 on the landing pad 109.

In a first example scenario, the vehicle sanitizer system 108 may open one or more windows of the motor vehicle 105 after detecting a landing of the UAV 130 on the landing pad 109. In a second example scenario, the vehicle sanitizer system 108 may open one or more windows of the motor vehicle 105 prior to the UAV 130 landing on the landing pad 109. The window opening operation in this second scenario may be based on an expected time of arrival (ETA) of the UAV 130. The ETA may be determined via communications between the vehicle sanitizer system 108 of the motor vehicle 105 and the vehicle sanitizer service system 134 of the UAV 130.

After landing on the landing pad 109, the UAV 130 may insert an articulated arm 132 through the open window for executing a sanitizing procedure of the cabin area of the motor vehicle 105. In some cases, the UAV 130 may have multiple articulated arms and these multiple articulated arms may be inserted into the cabin area through one or more open windows. The insertion of the multiple articulated arms may be carried out concurrently/simultaneously through multiple open windows, or sequentially through one open window.

The sanitization procedure can include one or more operations such as, for example, dispensing an aerosol (disinfectant, deodorizer, air freshener, etc.) in the cabin area of the motor vehicle 105, dispensing a liquid or a gel upon a surface (seat, dashboard etc.), and/or scrubbing a surface (seat, dashboard etc.) with a sanitizing agent (a liquid soap, a disinfectant, a sterilizer, an antiseptic, etc.). The sanitizing agents (disinfectant, sterilizer, antiseptic, deodorizer, soap, etc.) may be selected on the basis of various factors. In one case, the sanitizing agents may be selected on the basis of their cleaning characteristics and the type of pollutants present in the cabin area (dirt, liquid stains, viruses, bacteria, allergens etc.). In another case, the sanitizing agents may be selected on the basis of a season. A first sanitizing agent may be selected during the spring season, for example, for purposes of removing allergens that may be present in the cabin area. A second sanitizing agent may be selected during the winter season, for example, for purposes of eliminating pathogens (flu virus, COVID-19 virus, bacteria, etc.) that may be present in the cabin area.

In an example implementation, the articulated arm 132 may include one or more sensors and/or a camera that may be used to obtain data and/or images of various objects located in the cabin area of the motor vehicle 105. The data and/or images may be evaluated by the vehicle sanitizer service system 134 of the UAV 130 for various reasons. For example, data/image evaluation may be carried out in order to identify the layout of various objects (seats, occupants (if any), etc.) in the cabin area of the motor vehicle 105. The layout may then be used by the vehicle sanitizer service system 134 of the UAV 130 to plan a motion path and/or a sequence of actions that the articulated arm may carry out during a sanitizing procedure of the cabin area.

As another example, data/image evaluation may be carried out in order to detect a level of pollutants that may be present inside the cabin area of the motor vehicle before, and/or after, a sanitizing procedure has been executed. A level of cleanliness of the cabin area may be determined by the vehicle sanitizer service system 134 in the UAV 130 by comparing a detected level of pollutants in the cabin area to a threshold level that may be stored in a database. The sanitizing procedure may be terminated when the level of pollutants is below the threshold level.

Figure 2:
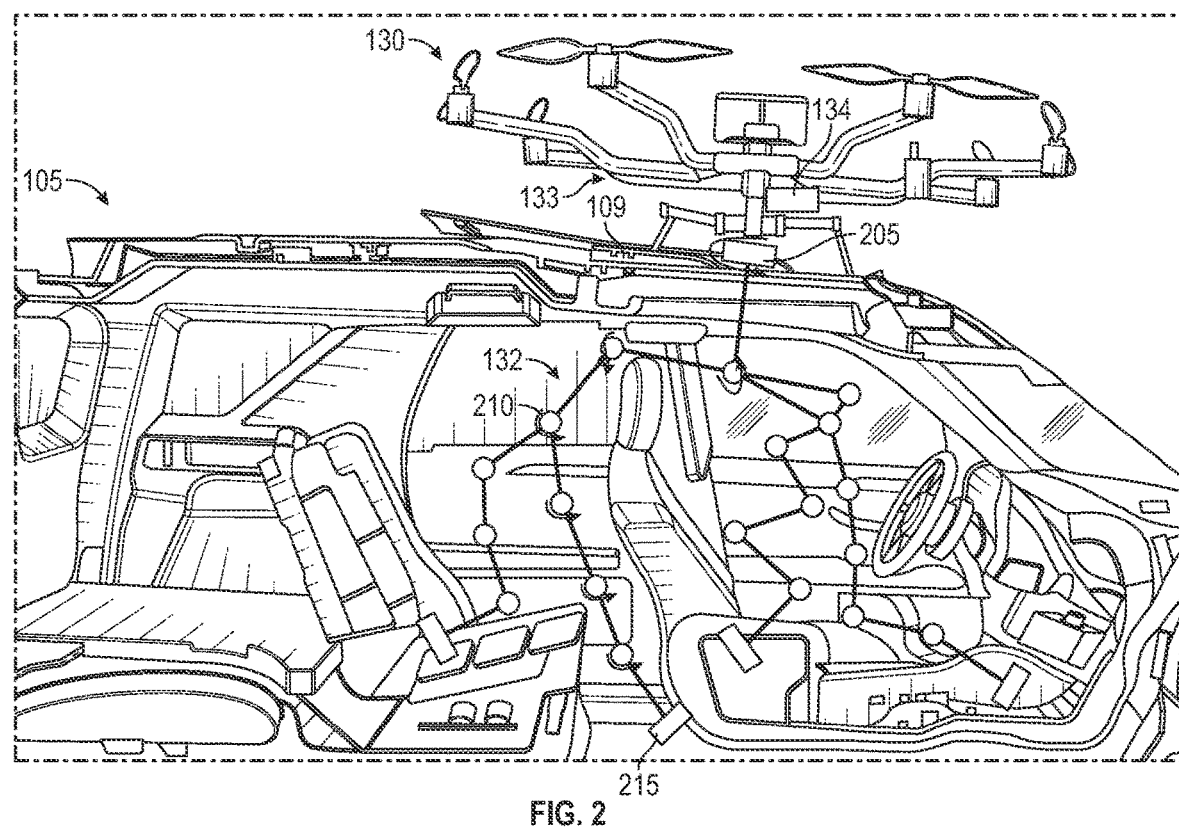
FIG. 2 illustrates an UAV that has landed upon the roof of a motor vehicle and in accordance with an embodiment of the disclosure.

FIG. 2 illustrates the UAV 130 after landing upon the roof of the motor vehicle 105 in accordance with an embodiment of the disclosure. The UAV 130 is anchored in position by activation of the various latches (electromagnetic latch 113, electromagnetic latch 114, etc.) provided on the landing pad 109 of the motor vehicle 105 and the various latches (electromagnetic latch 131, electromagnetic latch 136, etc.) provided in the landing gear of the UAV 130. In an example implementation, a charging cable (not shown) may be provided in the UAV 130. The vehicle sanitizer service system 134 may activate one or more motors and other elements to couple the charging cable to a battery charging socket provided on the landing pad 109 of the motor vehicle 105. A battery of the UAV 130 may be charged while the UAV 130 is docked upon the landing pad 109.

A servomotor 205 coupled to the articulated arm 132 of the UAV 130 can be operated by the vehicle sanitizer service system 134 for rotating the articulated arm 132 into a position that allows for insertion of the articulated arm 132 into an open window of the motor vehicle 105. Any suitable window of the motor vehicle 105 (such as, for example, on the left side of the motor vehicle 105, on the right side of the motor vehicle 105, or in the rear of the motor vehicle 105) may be opened by the vehicle sanitizer system 108 of the motor vehicle 105 to allow the articulated arm 132 to enter the cabin area. The articulated arm 132 may include one or more rotatable elbows (such as an example elbow 210) that accommodate bending of the articulated arm 132 into various shapes for cleaning various objects.

In the example implementation illustrated in FIG. 2, the articulated arm 132 may include a camera 215 configured to capture images of various objects located in the cabin area of the motor vehicle 105. The articulated arm 132 is shown in a first position for sanitizing a rear portion of the cabin area of the motor vehicle 105. The dotted line illustrations of the articulated arm 132 indicate other positions, movement paths, and orientations of the articulated arm 132 when sanitizing other portions of the cabin area.

Figure 3:
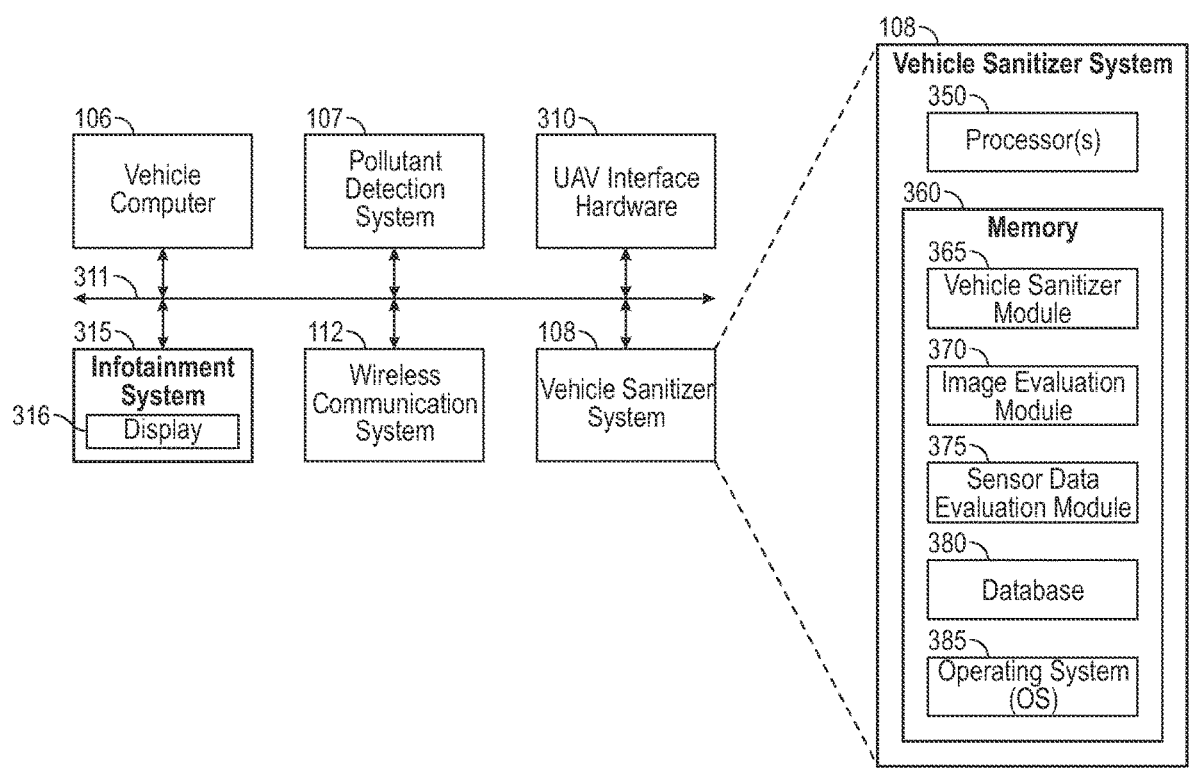
FIG. 3 shows some example components that may be included in a motor vehicle in accordance with an embodiment of the disclosure.

FIG. 3 shows some example components that may be included in the motor vehicle 105 in accordance with an embodiment of the disclosure. In this example configuration, the motor vehicle 105 may include the vehicle computer 106, the pollutant detection system 107, UAV interface hardware 310, an infotainment system 315, the wireless communication system 112, and the vehicle sanitizer system 108, which are communicatively coupled to each other via a bus 311.

The bus 311 can be implemented using one or more of various wired and/or wireless technologies. For example, the bus 311 can be a vehicle bus that uses a controller area network (CAN) bus protocol, a Media Oriented Systems Transport (MOST) bus protocol, and/or a CAN flexible data (CAN-FD) bus protocol. Some or all portions of the bus 311 may also be implemented using wireless technologies such as Bluetooth®, ZigBee®, or near-field-communications (NFC), cellular, Wi-Fi, Wi-Fi direct, machine-to-machine communication, and/or man-to-machine communication to accommodate communications between the vehicle sanitizer system 108 and the various other devices coupled to the bus 311.

The bidirectional links between the various devices can carry commands in one direction (such as, for example, a "fetch information" command issued by the vehicle sanitizer system 108 to the pollutant detection system 107 or a command to an element of the UAV interface hardware 310) and can carry information in an opposite direction (such as, for example, images and/or information from the pollutant detection system 107 to the vehicle sanitizer system 108).

The pollutant detection system 107 may include various types of components based on the nature of the detection process. For example, in one implementation, the pollutant detection system 107 may include one or more cameras that capture images of various objects in the cabin area of the motor vehicle 105 and provide the images to the vehicle sanitizer system 108 for evaluating. In another implementation, the pollutant detection system 107 may incorporate photodiode sensors and photodiode transmitters in an arrangement for detecting a level of pollutants that may be present on various objects in the cabin area of the motor vehicle 105.

The UAV interface hardware 310 may include various systems such as, for example, a UAV detection system, a window activator system, and hardware associated with the landing pad 109. The UAV detection system can include detection devices such as, for example, a camera, a weight sensor, an infrared detector, a radar detector, and/or a light detection and ranging (LIDAR) detector, configured to detect the UAV 130. The UAV 130 may be detected by the UAV detection system at various instants such as, for example, when approaching the motor vehicle 105 and/or upon landing upon the landing pad 109 provided on the roof of the motor vehicle 105. The hardware associated with the landing pad 109 can include items such as, for example, servomotors and latch activating devices that operate under control of the vehicle sanitizer system 108 to anchor the landing gear of the UAV 130 when the UAV 130 has landed on the roof of the motor vehicle 105. The window activator system can cooperate with the vehicle computer 106 to open one or more windows of the motor vehicle 105 upon receiving a command from the vehicle sanitizer system 108.

The wireless communication system 112 may include elements such as wireless transmitters and receivers that enable communicative coupling between the vehicle sanitizer system 108 and the network 150.

The infotainment system 315 can be an integrated unit that includes various components such as a radio, streaming audio solutions, and USB access ports for digital audio devices, with elements such as a navigation system that provides navigation instructions to a driver of the car and/or to the vehicle sanitizer system 108. In an example implementation, the infotainment system 315 has a display 316 that includes a graphical user interface (GUI) for use by an occupant of the motor vehicle 105. The GUI may be used for various purposes such as to allow the driver 116 of the motor vehicle 105 to make a request to sanitize the motor vehicle 105. The display 316 may also be employed by the vehicle sanitizer system 108 to display various types of alerts and messages associated with washing the motor vehicle 105. The vehicle sanitizer system 108, may, for example, instruct the driver 116 to open a window when the UAV 130 has landed (or is expected to land) on the roof of the motor vehicle 105. The vehicle sanitizer system 108, may, further instruct the driver 116 to leave the window open and exit the motor vehicle 105 so as to allow the UAV 130 to sanitize the cabin area of the motor vehicle 105.

The GUI may be omitted in implementations where the motor vehicle 105 is an autonomous vehicle. In this scenario, the vehicle sanitizer system 108 may evaluate data and/or images received from the pollutant detection system 107 and make a determination that the cabin area is in need of sanitization. In one case, the autonomous vehicle may be a ride share vehicle and the need for sanitization may arise as a result of the pollutant detection system 107 detecting the presence of a virus in the cabin area after a ride share passenger has exited the motor vehicle 105 (leaving the cabin area unoccupied). The vehicle sanitizer system 108 may then communicate with the wireless communications system 112 to transmit a sanitization request to the UAV 130 and/or the server computer 120. The vehicle sanitizer system 108 may further communicate with the vehicle computer 106 to instruct the vehicle computer 106 to activate a window motor to open a window of the motor vehicle 105. The UAV 130 may subsequently insert the articulated arm 132 through the open window.

The vehicle sanitizer system 108 may include a processor 350 and a memory 360. The memory 360, which is one example of a non-transitory computer-readable medium, may be used to store an operating system (OS) 385 and various code modules such as, for example, a vehicle sanitizer module 365, an image evaluation module 370, and a sensor data evaluation module 375. The code modules are provided in the form of computer-executable instructions that can be executed by the processor 350 for performing various operations in accordance with the disclosure.

The vehicle sanitizer module 365 may be executed by the processor 350 for performing various operations in accordance with the disclosure. These operations can include evaluating sensor data and/or camera images provided by the pollutant detection system 107 to the vehicle sanitizer system 108. The sensor data may be evaluated in cooperation with the sensor data evaluation module 375 for determining whether a level of pollutants present in the cabin area of the motor vehicle 105 exceeds a threshold value. The threshold value may be stored in a database 380. When the level of pollutants exceeds the threshold value, a remedial action directed at having the cabin area sanitized may be executed. The remedial action can include the vehicle sanitizer module 365 communicating with the wireless communication system 112 to transmit a request to sanitize the motor vehicle 105 and communicating with the vehicle computer 106 to open a window of the motor vehicle 105.

The database 380 may also contain various other data than can be made available to the vehicle sanitizer system 108 in the motor vehicle 105 and/or conveyed by the vehicle sanitizer system 108 to the vehicle sanitizer service system 134 of the UAV 130. One example of such data is vehicle identification data (a model and a make of the motor vehicle 105, for example).

Figure 4:
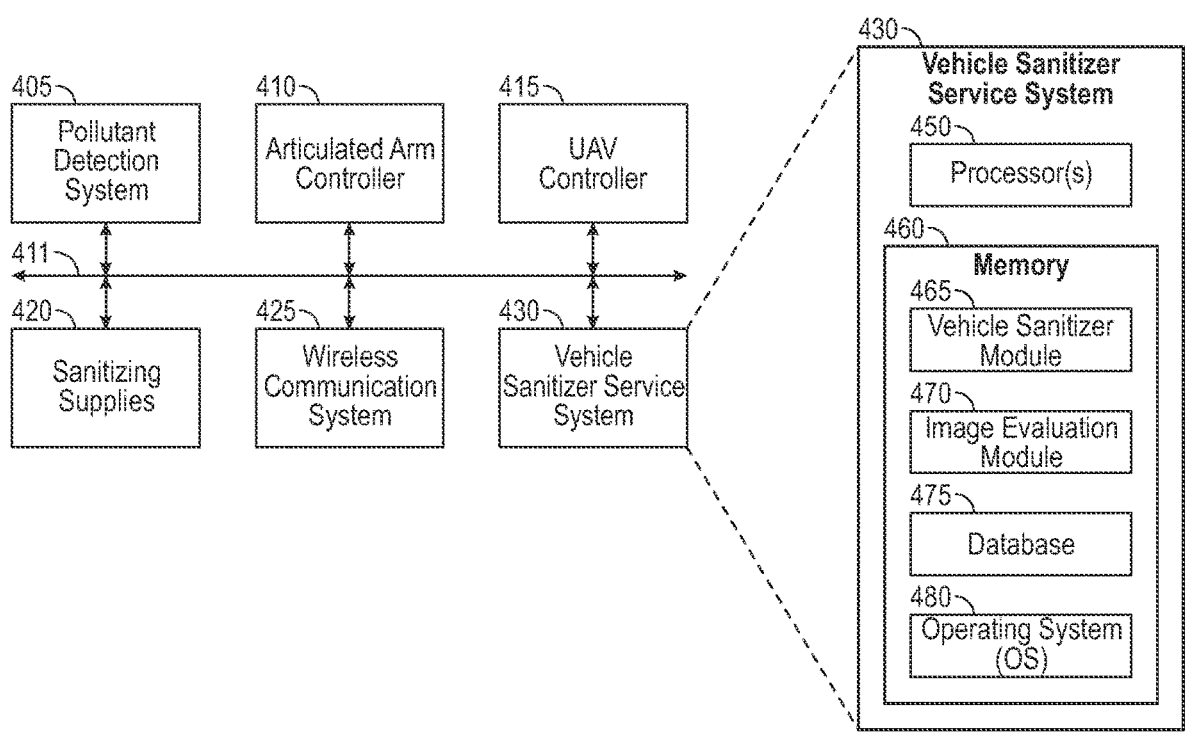
FIG. 4 shows some example components that may be included in an UAV in accordance with an embodiment of the disclosure.

FIG. 4 shows some example components that may be included in the UAV 130 in accordance with an embodiment of the disclosure. In this example configuration, the UAV 130 may include a pollutant detection system 405, an articulated arm controller 410, a UAV controller 415, a wireless communication system 425, sanitizing supplies 420, and the vehicle sanitizer service system 430, which are communicatively coupled to each other via a bus 411. The bus 411 can be implemented using one or more of various wired and/or wireless technologies such as those described above.

The pollutant detection system 405 may include various types of components based on the nature of the detection process. For example, in one implementation, the pollutant detection system 405 may include the camera 215 that is attached to the articulated arm 132 for detecting pollutants in the cabin area of the motor vehicle 105. In another implementation, the pollutant detection system 405 may include a sensor that is attached to the articulated arm 132 for detecting certain types of pollutants in the cabin area of the motor vehicle 105.

The articulated arm controller 410 controls various operations of the articulated arm 132 by providing control signals and commands to elements such as, for example, the servomotor 205 that is described above.

The UAV controller 415 may perform various functions such as, for example, controlling flight operations, navigation operations, and vehicle identification operations. In an example operation, the UAV controller 415 may operate the electromagnetic latch 131 and the electromagnetic latch 136 of the landing gear when the UAV 130 has landed upon the landing pad 109 of the motor vehicle 105.

The wireless communication system 425 may include elements such as wireless transmitters and receivers that enable communicative coupling between the UAV 130 and the network 150.

The sanitizing supplies 420 can include sanitizing agents (detergent, disinfectant, antiseptic, deodorizer, air freshener, cleaning liquid, chemicals for killing viruses, etc.) that can be accessed by the articulated arm 132 for sanitizing the motor vehicle 105.

The vehicle sanitizer service system 430 may include a processor 450 and a memory 460. The memory 460, which is another example of a non-transitory computer-readable medium, may be used to store an operating system (OS) 480 and various code modules such as, for example, a vehicle sanitizer module 465 and an image evaluation module 470. The code modules are provided in the form of computer-executable instructions that can be executed by the processor 450 for performing various operations in accordance with the disclosure.

The vehicle sanitizer module 465 may be executed by the processor 450 for performing various operations in accordance with the disclosure. These operations can include evaluating sensor data and/or camera images provided by the pollutant detection system 405 to the vehicle sanitizer service system 430. The camera images may be evaluated in cooperation with the image evaluation module 470 for determining whether a level of pollutants present in the cabin area of the motor vehicle 105 exceeds a threshold value. The threshold value may be stored in a database 475. When the level of pollutants exceeds the threshold value, a remedial action directed at having the cabin area sanitized may be executed. The remedial action can include the vehicle sanitizer module 465 communicating with the articulated arm controller 410 to dispense one or more sanitizing agents fetched from the sanitizing supplies 420.

The database 475 may also contain various other data than can be made available to the vehicle sanitizer service system 430 by the motor vehicle 105 and/or the server computer 120. One example of such data is vehicle identification data (a model and a make of the motor vehicle 105, for example).

FIG. 5 shows some example components that may be included in the personal communication device 111 (shown in FIG. 1) in accordance with an embodiment of the disclosure. The personal communication device 111 may include a processor 550 and a memory 555. The memory 555, which is yet another example of a non-transitory computer-readable medium, may be used to store an operating system (OS) 565 and various code modules such as, for example, a vehicle sanitization request module 560. The code modules are provided in the form of computer-executable instructions that can be executed by the processor 550 for performing various operations in accordance with the disclosure.

The vehicle sanitization request module 560, which may be downloaded into the personal communication device 111 in the form of a software application, may be executed by the processor 550 for performing various operations in accordance with the disclosure. In an example operation, the vehicle sanitization request module 560 may process a sanitization request entered into the personal communication device 111 by an individual (such as, for example, the driver 116 of a driver-operated vehicle or an occupant of an autonomous vehicle) and communicate with the UAV 130 and/or the server computer 120 to fulfil the request. The vehicle sanitization request module 560 may also display alerts and/or messages upon a display screen of the personal communication device 111. An example message may inform the individual to open a window of the motor vehicle 105 when the UAV 130 has landed (or is expected to land) on the roof of the motor vehicle 105. The vehicle sanitization request module 560 may further instruct the individual to leave the window open and exit the motor vehicle 105 so as to allow the UAV 130 to sanitize the cabin area of the motor vehicle 105.

In the above disclosure, reference has been made to the accompanying drawings, which form a part hereof, which illustrate specific implementations in which the present disclosure may be practiced. It is understood that other implementations may be utilized, and structural changes may be made without departing from the scope of the present disclosure. References in the specification to "one embodiment," "an embodiment," "an example embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, one skilled in the art will recognize such feature, structure, or characteristic in connection with other embodiments whether or not explicitly described.

Implementations of the systems, apparatuses, devices, and methods disclosed herein may comprise or utilize one or more devices that include hardware, such as, for example, one or more processors and system memory, as discussed herein. An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or any combination of hardwired or wireless) to a computer, the computer properly views the connection as a transmission medium. Transmission media can include a network and/or data links, which can be used to carry desired program code means in the form of computer-executable instructions or data structures and which can be accessed by a general purpose or special purpose computer. Combinations of the above should also be included within the scope of non-transitory computer-readable media.

Computer-executable instructions comprise, for example, instructions and data which, when executed at a processor, such as the processor 350, the processor 450, or the processor 550, cause the processor to perform a certain function or group of functions. The computer-executable instructions may be, for example, binaries, intermediate format instructions such as assembly language, or even source code.

Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

A memory device such as the memory 360, the memory 460, or the memory 555, can include any one memory element or a combination of volatile memory elements (e.g., random access memory (RAM, such as DRAM. SRAM, SDRAM, etc.)) and non-volatile memory elements (e.g., ROM, hard drive, tape, CDROM, etc.). Moreover, the memory device may incorporate electronic, electromagnetic, optical, and/or other types of storage media. In the context of this document, a "non-transitory computer-readable medium" can be, for example but not limited to, an electronic, electromagnetic, optical, electromagnetic, infrared, or semiconductor system, apparatus, or device. More specific examples (a non-exhaustive list) of the computer-readable medium would include the following: a portable computer diskette (electromagnetic), a random-access memory (RAM) (electronic), a read-only memory (ROM) (electronic), an erasable programmable read-only memory (EPROM. EEPROM, or Flash memory) (electronic), and a portable compact disc read-only memory (CD ROM) (optical). Note that the computer-readable medium could even be paper or another suitable medium upon which the program is printed, since the program can be electronically captured, for instance, via optical scanning of the paper or other medium, then compiled, interpreted or otherwise processed in a suitable manner if necessary, and then stored in a computer memory.

Those skilled in the art will appreciate that the present disclosure may be practiced in network computing environments with many types of computer system configurations, including in-dash vehicle computers, personal computers, desktop computers, laptop computers, message processors, handheld devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by any combination of hardwired and wireless data links) through a network, both perform tasks. In a distributed system environment, program modules may be located in both the local and remote memory storage devices.

Further, where appropriate, the functions described herein can be performed in one or more of hardware, software, firmware, digital components, or analog components. For example, one or more application specific integrated circuits (ASICs) can be programmed to carry out one or more of the systems and procedures described herein. Certain terms are used throughout the description, and claims refer to particular system components. As one skilled in the art will appreciate, components may be referred to by different names. This document does not intend to distinguish between components that differ in name, but not function.

It should be noted that the sensor embodiments discussed above may comprise computer hardware, software, firmware, or any combination thereof to perform at least a portion of their functions. For example, a sensor may include computer code configured to be executed in one or more processors and may include hardware logic/electrical circuitry controlled by the computer code. These example devices are provided herein for purposes of illustration and are not intended to be limiting. Embodiments of the present disclosure may be implemented in further types of devices, as would be known to persons skilled in the relevant art(s).

At least some embodiments of the present disclosure have been directed to computer program products comprising such logic (e.g., in the form of software) stored on any computer-usable medium. Such software, when executed in one or more data processing devices, causes a device to operate as described herein.

While various embodiments of the present disclosure have been described above, it should be understood that they have been presented by way of example only, and not limitation. It will be apparent to persons skilled in the relevant art that various changes in form and detail can be made therein without departing from the spirit and scope of the present disclosure. Thus, the breadth and scope of the present disclosure should not be limited by any of the above-described example embodiments but should be defined only in accordance with the following claims and their equivalents. The foregoing description has been presented for the purposes of illustration and description. It is not intended to be exhaustive or to limit the present disclosure to the precise form disclosed. Many modifications and variations are possible in light of the above teaching. Further, it should be noted that any or all of the aforementioned alternate implementations may be used in any combination desired to form additional hybrid implementations of the present disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could." "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

That which is claimed is:

1. A method comprising:

transmitting, by a vehicle, a request to sanitize the vehicle;

detecting, by the vehicle, an arrival of an unmanned aerial vehicle that is configured to sanitize the vehicle;

detecting, by the vehicle, a landing of the unmanned aerial vehicle upon a roof of the vehicle;

opening, by the vehicle, a window of the vehicle to allow entry of an articulated arm of the unmanned aerial vehicle into a cabin area of the vehicle while the unmanned aerial vehicle is landed on the roof of the vehicle; and detecting, by the vehicle, a completion of a sanitizing procedure of the cabin area of the vehicle by the unmanned aerial vehicle.

2. The method of claim 1, wherein the sanitizing procedure comprises dispensing one of a cleaning agent, a disinfectant, and/or an aerosol.

3. The method of claim 1, wherein the request includes a vehicle identification and a vehicle location to assist the unmanned aerial vehicle to rendezvous with the vehicle.

4. The method of claim 3, wherein the vehicle identification comprises a make and a model of the vehicle that is stored in a database and wherein the method further comprises:
obtaining, by the unmanned aerial vehicle, from the database, information comprising the make and model of the vehicle;
identifying, by the unmanned aerial vehicle, the vehicle based on the make and the model of the vehicle;
landing, by the unmanned aerial vehicle, upon the roof of the vehicle;
detecting, by the unmanned aerial vehicle, the window of the vehicle that is open; and
inserting, by the unmanned aerial vehicle while it is landed on the roof of the vehicle, based on the make and the model of the vehicle, the articulated arm of the unmanned aerial vehicle into the cabin area of the vehicle through the window.

5. The method of claim 4, wherein the unmanned aerial vehicle is programmed in accordance with the make and the model of the vehicle to maneuver the articulated arm inside the cabin area of the vehicle as a part of the sanitizing procedure.

6. The method of claim 5, wherein detecting, by the vehicle, completion of the sanitizing procedure of the cabin area of the vehicle by the unmanned aerial vehicle comprises:
detecting a level of pollutants present inside the cabin area of the vehicle; and
determining that the level of pollutants is below a threshold level.

7. A method comprising:
receiving, by an unmanned aerial vehicle, a request to sanitize a motor vehicle;
determining, by the unmanned aerial vehicle, a flight path to rendezvous with the motor vehicle;
landing, by the unmanned aerial vehicle, upon a roof of the motor vehicle;
detecting, by the unmanned aerial vehicle, an open window of the motor vehicle;
inserting, by the unmanned aerial vehicle while the unmanned aerial vehicle is landed on the roof of the motor vehicle, an articulated arm of the unmanned aerial vehicle into a cabin area of the motor vehicle through the open window; and
executing, by the unmanned aerial vehicle, a sanitizing procedure to sanitize the cabin area of the motor vehicle.

8. The method of claim 7, further comprising:
dispensing one of a cleaning agent, a disinfectant, and/or an aerosol inside the cabin area of the motor vehicle as a part of the sanitizing procedure.

9. The method of claim 7, wherein the request includes a vehicle identification and a vehicle location to assist the unmanned aerial vehicle to rendezvous with the motor vehicle, and wherein determining the flight path comprises:
obtaining, by the unmanned aerial vehicle, from a database, information comprising a make and a model of the motor vehicle;
identifying, by the unmanned aerial vehicle, the motor vehicle based on the make and model of the motor vehicle; and
configuring, by the unmanned aerial vehicle, based on the make and the model of the motor vehicle, the articulated arm of the unmanned aerial vehicle for entry of the articulated arm into the cabin area of the motor vehicle through the open window.

10. The method of claim 9, further comprising:
maneuvering, by the unmanned aerial vehicle, the articulated arm of the unmanned aerial vehicle through a pre-programmed path inside the cabin area of the motor vehicle for executing the sanitizing procedure.

11. The method of claim 10, wherein the pre-programmed path is based on the make and the model of the motor vehicle.

12. The method of claim 7, wherein receiving the request to sanitize the motor vehicle comprises receiving a wireless message directly from the motor vehicle or indirectly from a server computer.

13. A system comprising:
a vehicle, comprising:
a first communications system configured to transmit a wireless request to sanitize the vehicle;
an unmanned aerial vehicle (UAV) detector system configured to detect an arrival of a UAV that is configured to sanitize the vehicle;
a window activator system configured to open a window of the vehicle to allow entry of an articulated arm of the unmanned aerial vehicle into a cabin area of the vehicle while the unmanned aerial vehicle is landed on a roof of the vehicle; and
a pollutant detection system configured to detect a completion of a sanitizing procedure of the cabin area of the vehicle by the unmanned aerial vehicle.

14. The system of claim 13, wherein the unmanned aerial vehicle comprises:
a second communications system configured to wirelessly communicate with the first communication system in the vehicle; and
an articulated arm controller configured to operate the articulated arm to sanitize the cabin area of the vehicle.

15. The system of claim 14, wherein the second communications system is further configured to wirelessly communicate with a server computer for obtaining a vehicle identification and a vehicle location of the vehicle, and wherein the articulated arm controller is configured to maneuver the articulated arm for entry into the cabin area of the vehicle through the window of the vehicle.

16. The system of claim 15, wherein the articulated arm controller is further configured to maneuver the articulated arm through a pre-programmed path inside the cabin area of the vehicle for executing the sanitizing procedure.

17. The system of claim 14, wherein the vehicle includes a landing pad on a roof of the vehicle, the landing pad comprising a first electromagnetic latch configured to anchor a second electromagnetic latch that is provided in a landing gear of the unmanned aerial vehicle.

18. The system of claim 14, wherein the articulated arm of the unmanned aerial vehicle is configured to hold one of a can, a brush, and/or a scrubbing pad.

19. The system of claim 14, wherein the vehicle is an autonomous vehicle and the first communications system is configured to transmit the wireless request to sanitize the vehicle in response to receiving a signal from the pollutant detection system based on detecting a first level of pollutants present inside the cabin area of the vehicle.

\* \* \* \* \*